(12) United States Patent
Kim et al.

(10) Patent No.: US 12,005,264 B2
(45) Date of Patent: Jun. 11, 2024

(54) SKIN CARE DEVICE WITH PLASMA GENERATING DEVICE

(71) Applicant: GCS Co., Ltd., Seongnam-si (KR)

(72) Inventors: Chang Sik Kim, Gyeonggi-do (KR); Tae Yong Kim, Seoul (KR); Myeong Woo Kim, Gyeonggi-do (KR); Hyuk Namgoong, Gyeonggi-do (KR); Ha Yun Lee, Gyeonggi-do (KR)

(73) Assignee: GCS Co., Ltd., Seongnam-si (KR)

( * ) Notice: Subject to any disclaimer, the term of this patent is extended or adjusted under 35 U.S.C. 154(b) by 0 days.

(21) Appl. No.: 18/230,168

(22) Filed: Aug. 4, 2023

(65) Prior Publication Data

US 2024/0042223 A1    Feb. 8, 2024

(30) Foreign Application Priority Data

Aug. 5, 2022    (KR) .................... 10-2022-0097827

(51) Int. Cl.
| | | |
|---|---|---|
| *A61N 1/04* | (2006.01) | |
| *A61N 1/08* | (2006.01) | |
| *A61N 1/44* | (2006.01) | |
| *B01D 53/04* | (2006.01) | |
| *H05H 1/24* | (2006.01) | |

(52) U.S. Cl.
CPC .............. *A61N 1/44* (2013.01); *A61N 1/0476* (2013.01); *A61N 1/08* (2013.01); *B01D 53/0446* (2013.01); *H05H 1/24* (2013.01); *B01D 2253/102* (2013.01); *B01D 2257/106* (2013.01); *B01D 2259/455* (2013.01); *H05H 2245/10* (2021.05); *H05H 2245/34* (2021.05)

(58) Field of Classification Search
CPC .......... A61N 1/44; A61N 1/0476; A61N 1/08; B01D 53/0446; B01D 2253/102; B01D 2257/106; B01D 2259/455; H05H 1/24; H05H 2245/10; H05H 2245/34
See application file for complete search history.

(56) References Cited

U.S. PATENT DOCUMENTS 11,529,181 B2 * 12/2022 Ahn ..................... A61N 1/44
2023/0010556 A1 * 1/2023 Gu .................. A61M 37/0015

FOREIGN PATENT DOCUMENTS

| | | |
|---|---|---|
| KR | 10-2005-0077154 A | 8/2005 |
| KR | 10-2019-0041874 A | 4/2019 |
| KR | 10-2019-0141043 A | 12/2019 |
| KR | 10-2021-0150764 A | 12/2021 |
| KR | 20210150764 A | * 12/2021 |

* cited by examiner

*Primary Examiner* — Deanna K Hall
(74) *Attorney, Agent, or Firm* — Nicholas Park

(57) ABSTRACT

Disclosed is a skin care device using plasma. The skin care device may include a first plasma generating device; and a main body configured to supply power to the first plasma generating device and to control the first plasma generating device based on an input from a user.

15 Claims, 14 Drawing Sheets

SKIN CARE DEVICE WITH PLASMA GENERATING DEVICE

CROSS-REFERENCE TO RELATED APPLICATION

This application claims priority from and the benefit of Korean Patent Application No. 10-2022-0097827 filed on Aug. 5, 2022, which is hereby incorporated by reference in its entirety.

BACKGROUND

Technical Field

The present disclosure relates to a skin care device and more particularly, to a skin care device for irradiating plasma to a human body using a plasma generating device.

Related Art

People living in modern times do not mind investing a lot of money, time, and effort for beauty. One example for beauty may include skin beauty. Since the skin is usually shown first for people, the people invest a lot of money in skin care.

Devices for beauty may include devices using laser, ultrasound, or plasma. In particular, there may be a recent trend that the number of devices using plasma is increasing.

Plasma is an ionized gas and may be a fourth state of a material following solid, liquid, and gas. In general, plasma may be generated based on discharge of high voltage and may be used for the purpose of treatment and shaping of an epidermal portion of the skin due to a sublimation action occurring when induced on the skin of a user. Here, the sublimation action may refer to a phase transition phenomenon in which a substance changes from a solid to a gas without going through a liquid process in chemistry.

Since plasma is generated based on discharge of high voltage, devices using plasma may be formed as a single set with a separately provided power supply source to be stably supplied with power. However, as the power supply source and the devices using the plasma are formed as a single set, the user (e.g., an operator) needs to have several sets of devices and power supply sources to perform an appropriate procedure on a human body of a customer. This forced the user to make a lot of financial investment and eventually caused a lot of cost to be charged to the customer.

Reference material includes Korean Patent Laid-Open Publication No. 10-2005-0077154.

SUMMARY

The present disclosure is conceived to outperform the aforementioned related art and provides a skin care device that allows replacement of various plasma generating devices.

Technical objects set forth herein are not limited to the aforementioned technical objects and other technical objects not described herein may be clearly understood by one of ordinary skill in the art from the following description.

According to an example embodiment of the present disclosure to solve the aforementioned objects, there is provided a skin care device using plasma, the skin scare device including a first plasma generating device; and a main body configured to supply power to the first plasma generating device and to control the first plasma generating device based on an input from a user, wherein the first plasma generating device includes a first gripping portion configured to detachably connect to the main body, including a plasma generating portion for generating the plasma, and formed in a shape capable of being gripped by the user; and a first operating portion provided at one end of the first gripping portion and configured to discharge the plasma over a predetermined area, and the first operating portion includes a first housing having a plurality of pins for irradiating the plasma to a human body; a second housing to which the first housing couples, and formed with a hollow through which the plurality of pins pass in response to coupling of the first housing; and a third housing configured to couple to the second housing and protect the plurality of pins from an outside.

Also, the main body may include a first interface unit configured to receive the input from the user; and a first ozone removal portion configured to remove ozone that is generated as the plasma is irradiated to the human body.

Also, the first ozone removal portion may include an air pump configured to suck the ozone; and a first air hose of which one end is connected to the air pump and of which another end is connected to a second air hose provided to the first plasma generating device.

Also, the first gripping portion may further include a fastener configured to detachably connect the first air hose.

Also, the plasma generating portion may include a switch unit including a plurality of electrodes and configured to control the plurality of electrodes based on the input from the user; a plurality of transformers configured to boost voltage transmitted from the plurality of electrodes; and a plasma padder configured to transmit the voltage boosted by the plurality of transformers to the plurality of pins.

Also, the number of the plurality of transformers may be less than or equal to the number of the plurality of pins.

Also, the switch unit may be configured to apply voltage to at least one transformer through at least some electrodes among the plurality of electrodes based on the input from the user, and the at least one transformer may be configured to boost the applied voltage and to transmit the boosted voltage to at least one pin through the plasma padder.

Also, the first gripping portion may further include a second ozone removal portion configured to remove ozone ($O_3$) that is generated as the plasma is irradiated to the human body.

Also, the second ozone removal portion may include a suction fan configured to suck the ozone; and an ozone filter configured to remove the sucked ozone.

Also, the second housing may include a case portion configured to form at least a portion of an appearance of the second housing, the case portion including a first surface that forms one surface in a direction in which the third housing is located and a second surface that extends from a first circumference of the first surface in a direction opposite to the direction in which the third housing is located; and a protruding portion configured to protrude from the first surface, the protruding portion protruding from the first surface to have a second circumference less than the first circumference of the first surface.

Also, the hollow formed to allow the plurality of pins to pass may be provided to the protruding portion, a plurality of suction holes through which the ozone is sucked as the suction fan operates may be formed in the first surface, and a plurality of discharge holes through which the ozone is discharged may be formed in at least one region of the second surface.

Also, the third housing may be formed with a plurality of holes in a third surface that faces the human body, such that the plasma discharged from the plurality of pins is irradiated to the human body.

Also, the number of the plurality of holes may correspond to the number of the plurality of pins.

Also, the third housing may include at least one space maintaining portion configured to protrude from the third surface and to maintain a space between the third surface and the human body.

Also, the skin care device may further include a skin cooling device including a second operating portion configured to detachably couple to the main body and to cool the human body through a Peltier element that generates Peltier effect.

Also, the skin care device may further include a second plasma generating device including a plasma generating portion configured to detachably couple to the main body and to generate plasma, a second gripping portion formed in a shape capable of being gripped by the user, and a third operating portion provided at one end of the second gripping portion and configured to discharge the plasma to one point.

Technical solutions achievable from the present disclosure are not limited to the aforementioned solutions and other solutions not described herein may be clearly understood by one of ordinary skill in the art to which the present disclosure pertains from the following description.

According to some example embodiments of the present disclosure, it is possible to provide a skin care device capable of performing various procedures.

Effects achievable from the present disclosure are not limited to the aforementioned effects and other effects not described herein may be clearly understood by one of ordinary skill in the art to which the present disclosure pertains from the following description.

BRIEF DESCRIPTION OF THE FIGURES

Various aspects are described with reference to the accompanying drawings and, herein, like reference numerals refer to like elements throughout. In the following example embodiments, numerous specific details are set forth herein to provide thorough understanding of at least one aspect for the purpose of explanation. However, it will be apparent that such aspect(s) may be practiced without the specific details. In other examples, known structures and devices are illustrated in a form of a block diagram to easily describe at least one aspect.

DETAILED DESCRIPTION

Figure 1:
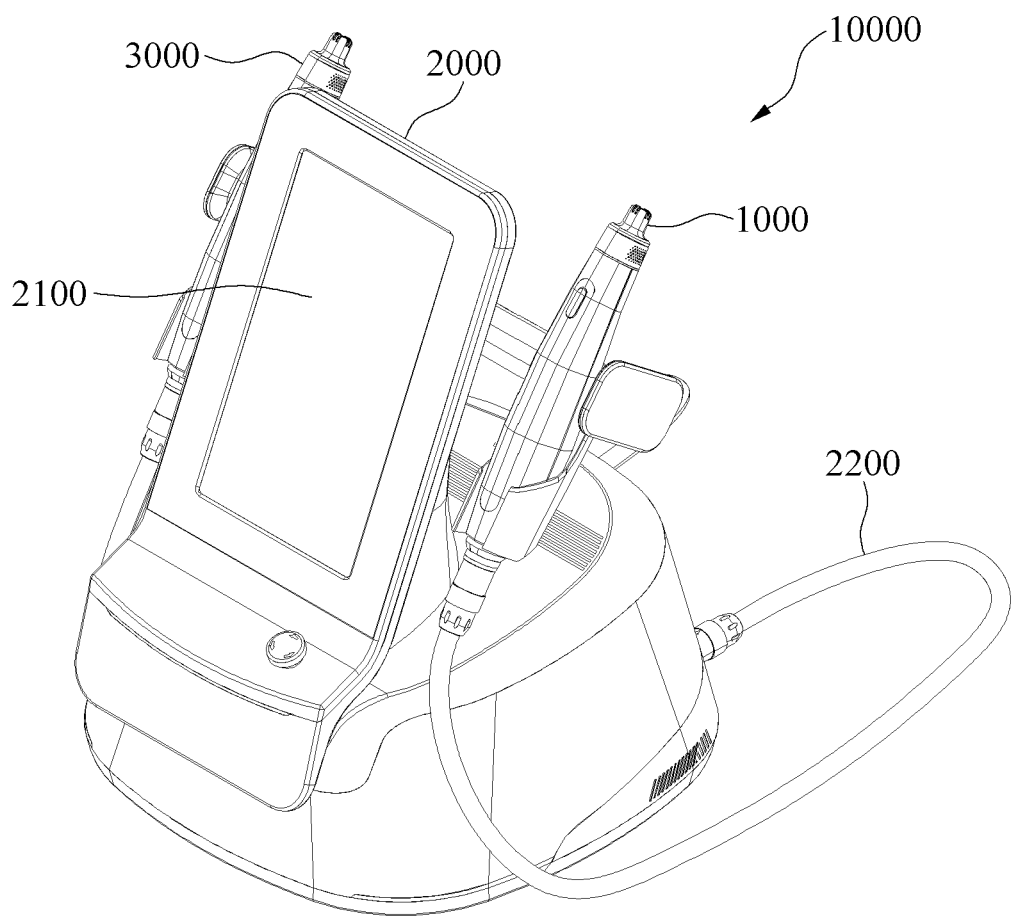
FIG. 1 is a perspective view illustrating an example of a skin care device according to some example embodiments of the present disclosure.

Various modifications and changes may be made to the present disclosure and the disclosure may include various example embodiments. Specific example embodiments are described in detail with reference to the accompanying drawings. The example embodiments, however, may be embodied in various different forms, and should not be construed as being limited to only the specific example embodiments. Rather, the example embodiments should be understood to include all of the modifications, equivalents, and substitutions included in the spirit and technical scope of the disclosure. Like reference numerals refer to like elements throughout to describe each drawing.

Although the terms "first," "second," "A," "B," etc., may be used herein to describe various components, the components should not be limited by these terms. These terms are only used to distinguish one component from another component. For example, a first component may also be termed a second component and, likewise, a second component may be termed a first component, without departing from the scope of this disclosure. As used herein, the term "and/or" includes any and all combinations of one or more of the associated items.

When a component is referred to as being "connected to" or "accessed to" another component, the component may be directly connected to or accessed to the other component, or one or more other intervening components may be present. In contrast, when a component is referred to as being "directly connected to" or "directly accessed to," there is no intervening component.

The terms used herein are used to simply explain specific example embodiments and are not construed to limit the present disclosure. The singular forms "a," "an," and "the," are intended to include the plural forms as well, unless the context clearly indicates otherwise. It will be further understood that the terms "comprises/comprising (incudes/including)," and "has/having" when used in this specification, specify the presence of stated features, integers, steps, operations, elements, and/or components, but do not preclude the presence or addition of one or more other features, integers, steps, operations, elements, components, and/or groups, thereof.

Unless otherwise defined, all terms including technical and scientific terms used herein have the same meaning as commonly understood by one of ordinary skill in the art to which the present disclosure pertains. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Herein, a skin care device may include a plasma generating device and a main body. The plasma generating device may be a device for a user to (e.g., operator) to irradiate plasma to a human body of another user (e.g., customer). Alternatively, the plasma generating device may be a device for the user to directly irradiate plasma to the user's own body. The user may remove blemishes, moles, or freckles by irradiating plasma to the skin of the customer or the user through the plasma generating device. Alternatively, the user may heal a wound or perform hemostasis by irradiating plasma to the skin of the customer or the user through the plasma generating device. Alternatively, the user may whiten teeth by irradiating plasma to teeth of the customer or the user through the plasma generating device.

Meanwhile, according to some example embodiments of the present disclosure, the skin care device may couple to various plasma generating devices in replaceable manner to perform procedures on a human body for various purposes. For example, the skin care device may include the plasma generating device for irradiating plasma to one point of the human body. Alternatively, the skin care device may include another plasma generating device for irradiating plasma to the human body over a larger area than the plasma generating device. Alternatively, the skin care device may include still another plasma generating device for cooling the sin before or after irradiating plasma to the skin. The user may perform an appropriate procedure using the aforementioned several plasma generating devices. Hereinafter, the skin care device according to the present disclosure is described with reference to FIGS. 1 to 12.

Figure 2:
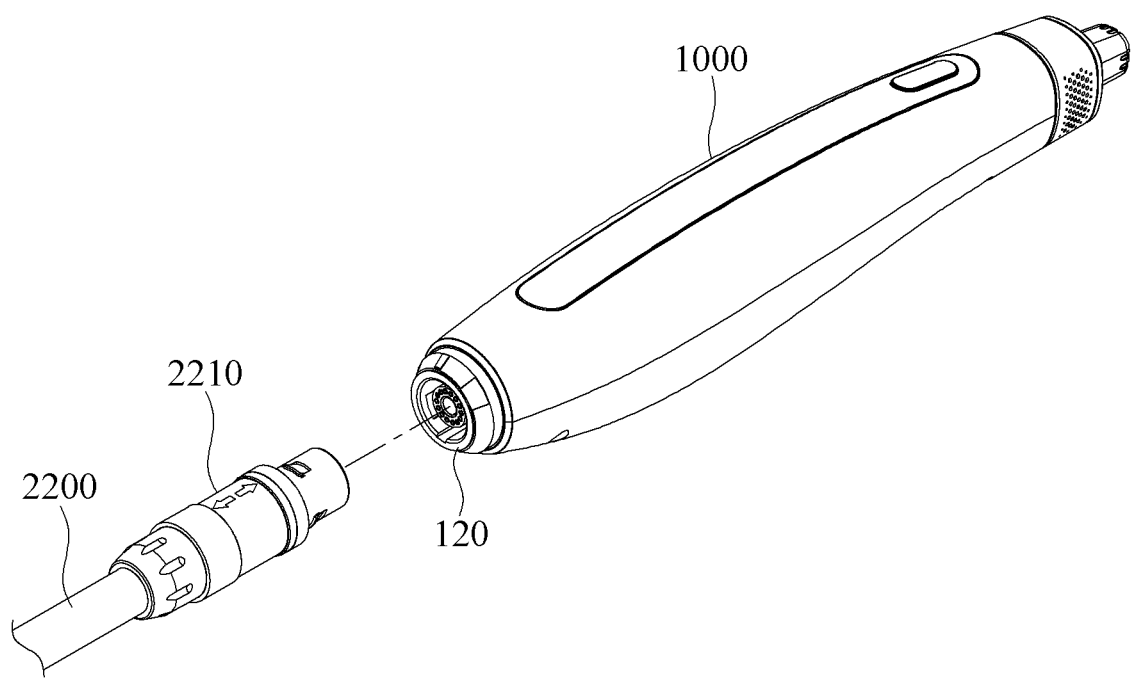
FIG. 2 is a perspective view illustrating a connection relationship between a plasma generating device and a main body according to some example embodiments of the present disclosure.

FIG. 1 is a perspective view illustrating an example of a skin care device according to some example embodiments of the present disclosure. FIG. 2 is a perspective view illustrating a connection relationship between a plasma generating device and a main body according to some example embodiments of the present disclosure.

Referring to FIG. 1, a skin care device 10000 may include a first plasma generating device 1000, a main body 2000, and a skin cooling device 3000. Here, the aforementioned components are not essential for implementing the skin care device 10000 and the skin care device 10000 may include more or fewer components than the components listed above.

The first plasma generating device 1000 may be a device that generates plasma to perform a procedure on a human body. The first plasma generating device 1000 may be a device for discharging plasma over a predetermined area.

The skin cooling device 3000 may be a device for performing another procedure on the human body. The skin cooling device 3000 may cool the human body through a Peltier element that generates Peltier effect. Here, the Peltier effect may be effect in which cooling occurs since electrons carry energy required to move from one metal surface to the other metal surface when current flows in a loop formed by mutually grounding metals through a semiconductor. The Peltier element may be an electronic material using the Peltier effect. The Peltier element according to the present disclosure may use the conventional art and thus, further description is omitted.

According to some example embodiments of the present disclosure, the skin care device 10000 may further include a second plasma generating device and a third plasma generating device. The second plasma generating device may be a device that discharges plasma to one point. The third plasma generating device may be a device that discharges relatively weak plasma compared to the first plasma generating device 1000 and the second plasma generating device. Hereinafter, examples of plasma devices according to the present disclosure are described below.

A main body 2000 may supply power to the plasma generating device connected to the main body 2000 and may control the plasma generating device based on an input from a user.

The main body 2000 may include a first interface unit 2100 configured to receive the input from the user.

The first interface unit 2100 may receive the input from the user for controlling the plasma generating device. The first interface unit 2100 may include a display implemented as a touch pad (static pressure/capacitive). In this case, the first interface unit 2100 may display (output) information processed by the main body 2000 and the plasma generating device. For example, the first interface unit 2100 may display execution screen information of an application program that runs on the main body 2000 or user interface (UI) information and graphic user interface (GUI) information according to the execution screen information.

Herein, the main body 2000 may include a first ozone removal portion (not shown) configured to remove ozone ($O_3$) that is generated as plasma is irradiated to the human body through the plasma generating device.

In detail, in the case of irradiating plasma to the skin through the plasma generating device, ozone that has adverse effect on a human may be generated. To prevent this, the main body 2000 may include the first ozone removal portion.

The first ozone removal portion may include an air pump provided in the main body 2000 and a first air hose 2200 configured to connect to the plasma generating device. The first air hose 2200 may be connected to the plasma generating device through an adaptor provided at its one end. As the first air hose 2200 is connected to the plasma generating device through the adaptor, the plasma generating device may be detachably connected to the main body 2000.

In detail, referring to FIG. 2, the adaptor 2210 may be provided at one end of the first air hose 2200. The first plasma generating device 1000 may include a fastener 120 to which the adaptor 2210 couples. The user may detachably connect the first air hose 2200 and the first plasma generating device 1000 through the fastener 120 and the adaptor 2210. Through this, the user may replace the plasma generating device. For example, the user may use the skin cooling device 3000 by separating the first plasma generating device 1000 and the first air hose 2200 and then coupling the skin cooling device 3000 and the first air hose 2200.

When the first air hose 2200 couples to the first plasma generating device 1000, the air pump may suck ozone that is generated according to operation of the first plasma generating device 1000. Therefore, ozone that may have adverse effect on a human may be removed. Hereinafter, an example of coupling the first air hose 2200 and the first plasma generating device 1000 is further described with reference to FIG. 9.

According to the aforementioned configuration, the skin care device 10000 may include the main body 2000 and plasma generating devices configured to detachably couple to the main body 2000. The user may perform an appropriate procedure on a customer using the plasma generating devices configured to detachably couple to the main body 2000. Hereinafter, the plasma generating devices according to the present disclosure are described.

Figure 3:
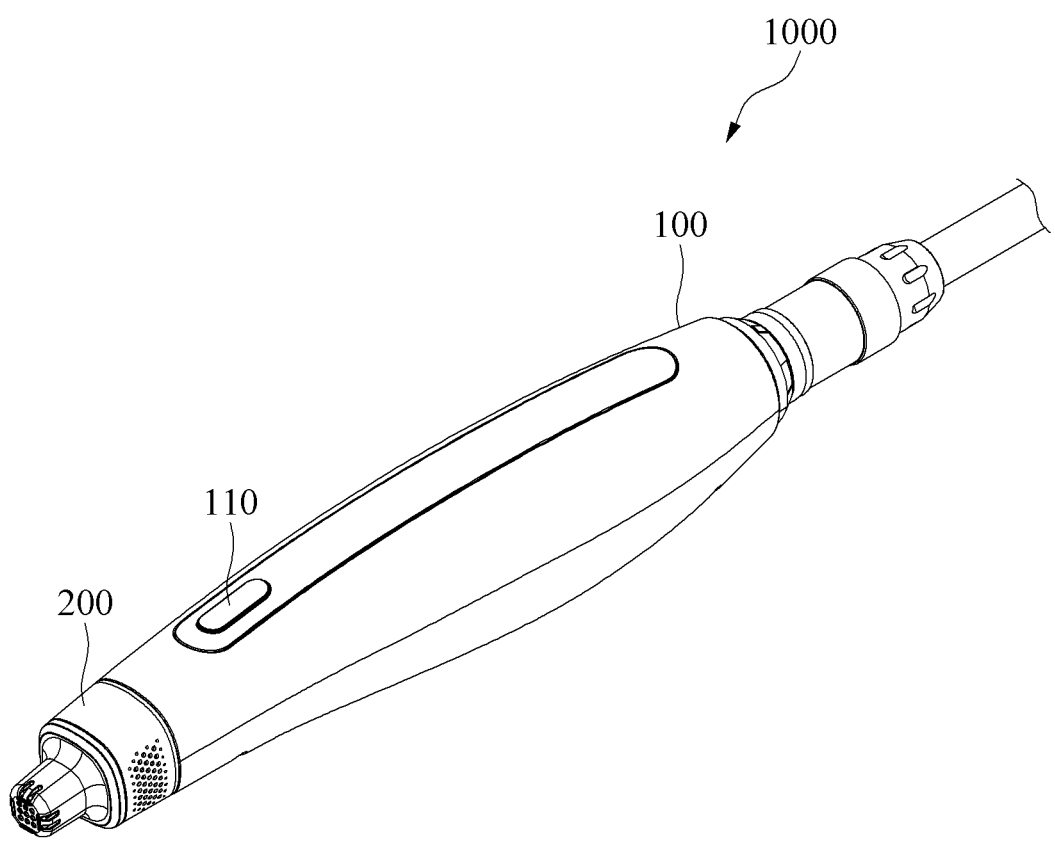
FIG. 3 is a perspective view illustrating a first plasma generating device according to some example embodiments of the present disclosure.

FIG. 3 is a perspective view illustrating a first plasma generating device according to some example embodiments of the present disclosure.

Referring to FIG. 3, the first plasma generating device 1000 may include a first gripping portion 100 and a first operating portion 200.

The first gripping portion 100 may be formed in a shape capable of being gripped by the user. The first gripping portion 100 may be formed in a shape that allows the user to easily grip the first plasma generating device 1000. According to an example embodiment, the first gripping portion 100 may be detachably connected to the main body 2000. For example, the first gripping portion 100 may be connected to the first air hose 2200 of the main body 2000 through the fastener 120.

The first gripping portion 100 may include a second interface unit 110 for receiving the input from the user, a plasma generating portion (not shown) for generating plasma, and a second ozone removal portion (not shown).

The second interface unit 110 may be implemented as at least one of a key pad, a dome switch, a touch pad (static pressure/capacitive), a jog wheel, and a jog switch. The second interface unit 110 may receive the input from the user for controlling the first plasma generating device 1000. For example, the second interface unit 110 may receive the input from the user for irradiating plasma.

The plasma generating portion may generate plasma based on the input from the user through the second interface unit 110. Alternatively, the plasma generating portion may generate plasma based on the input from the user through the first interface unit 2100.

The plasma generating portion may include a switch unit, a plurality of transformers, a transformer case, and a plasma padder. However, the aforementioned components are not essential to implement the plasma generating portion and thus, the plasma generating portion may include more or fewer components than the components listed above.

The switch unit may include a plurality of electrodes. The switch unit may control the plurality of electrodes based on the input from the user. For example, the switch unit may control the plurality of electrodes based on the input from the user through the first interface unit 2100 or the second interface unit 110.

According to some example embodiments of the present disclosure, the switch unit may independently turn ON/OFF each of the plurality of electrodes. For example, the switch unit may turn ON at least one electrode among the plurality of electrodes. The switch unit may turn OFF at least one electrode among the plurality of electrodes.

The plurality of transformers may boost voltage transmitted from the plurality of electrodes. The plurality of transformers may be a device that varies voltage using electromagnetic induction. The transformer may be understood as a transducer that boosts the voltage.

Each of the plurality of transformers may include a first core and a second core. Each of the plurality of transformers may further include a coil configured to wind around the first core and the second core.

The first core and the second core may be formed in a bar shape. The first core and the second core may have a solid cylindrical shape or a hollow cylindrical shape.

The first core and the second core may include a ferrite core or an iron core. One end of the first core may pass through a primary coil and another end thereof may pass through a secondary coil. Voltage applied to the primary coil of the first core may be boosted in the secondary coil. One end of the second core may pass through a (1-1)-order coil and another end thereof may pass through a (2-1)-order coil. Voltage applied to the (1-1)-order coil of the second core may be boosted in the (2-1)-order coil. Each of the plurality of transformers may boost the voltage transmitted from the plurality of electrodes through the first core and the second core in a stepwise manner.

The plurality of transformers according to the present disclosure may include the first core and the second core in the bar shape, which differs from an EI-type core. Accordingly, volume may be smaller than that of the conventional transformer and may be easily provided in a limited space inside the first gripping portion 100.

According to some example embodiments of the present disclosure, the number of the plurality of transformers may be less than or equal to the number of plurality of pins provided to the first operating portion 200. Here, the plurality of pins may be members that induce plasma generated from the plasma generating portion to be irradiated to the skin. For example, one end of each of the plurality of pins provided to the first operating portion 200 may be connected to the plasma generating portion to receive voltage. Another end of each of the plurality of pins extending from one end may be provided towards the human body. When the voltage is applied to one end of each of the plurality of pins, plasma may be generated between an end of each of the plurality of pins and the skin of the human body.

For example, if the number of plurality of pins is nine, the number of the plurality of transformers may be nine or less.

Depending on example embodiments, if the number of the plurality of transformers is less than the number of the plurality of pins, at least two pins among the plurality of pins may receive voltage from a single transformer. For example, the number of the plurality of transformers may be three. The number of the plurality of pins may be nine. In this case, three pins may receive voltage from a single transformer.

Each of the plurality of transformers may insert into the transformer case. The transformer case may include a plurality of holes for inserting the plurality of transformers, respectively. The plurality of transformers may insert into the plurality of holes, respectively.

The plasma padder may transmit the voltage boosted by the plurality of transformers to the plurality of pins. The plasma padder may include the plurality of electrodes for transmitting the voltage to the plurality of pins.

According to some example embodiments of the present disclosure, the switch unit may apply voltage to at least one transformer through at least some electrodes among the plurality of electrodes based on the input from the user. The at least one transformer may boost the applied voltage. The plasma padder may transmit the boosted voltage to the at least one pin. Therefore, the at least one pin that receives the voltage may irradiate plasma to the human body.

For example, the switch unit may independently turn ON/OFF each of the plurality of electrodes. The switch unit may apply voltage to three transformers through three electrodes among the plurality of electrodes. The three transformers to which the voltage is applied may boost the applied voltage and may transmit the boosted voltage to three electrodes included in the plasma padder. The three electrodes of the plasma padder may transmit the voltage to the plurality of pins connected to each electrode. For clarity of description, it is assumed that a single pin is connected to each of three electrodes. As three pins receive the voltage, plasma may be irradiated to the human body. That is, the user may irradiate plasma through at least one pin among the plurality of pins provided to the first operating portion 200. Therefore, if necessary, the user may irradiate plasma to a wide area using all of the plurality of pins or may irradiate plasma to a narrow area using at least one pin. Depending on example embodiments, output of plasma irradiated through at least one pin and output of plasma irradiated through the plurality of pins may differ from each other. The user may adjust the output by controlling an operation of the plurality of pins depending on necessity.

According to some example embodiments of the present disclosure, the number of the plurality of electrodes provided to the plasma padder may be less than or equal to the number of the plurality of pins. For example, if the number of the plurality of pins is nine, the number of the plurality of electrodes provided to the plasma padder may be nine or less. Meanwhile, if the number of the plurality of electrodes provided to the plasma padder is less than the number of plurality of pins, the plurality of pins may be connected to a single electrode. For example, the number of the plurality of electrodes provided to the plasma padder may be three and the number of the plurality of pins may be nine. In this case, three pins may be connected to each of three electrodes provided to the plasma padder.

According to some example embodiments of the present disclosure, the plurality of pins provided to the first operating portion 200 may receive only voltage without direct connection to the plasma padder. For example, the first operating portion 200 may include a printed circuit board (PCB) substrate for receive voltage from the plasma padder and transmitting the voltage to the plurality of pins. In this case, the plurality of pins may be connected to the PCB substrate. The PCB substrate may receive the voltage from the plasma padder or the plasma generating portion. The PCB voltage that receives the voltage may transmit the voltage to the plurality of pins.

According to some example embodiments of the present disclosure, at least some of components that constitute the plasma generating portion may be provided to the first operating portion 200. For example, the plasma padder may be provided to the first operating portion 200.

The second ozone removal portion may include a suction fan, an ozone filter, and a filter case. The second ozone removal portion may remove ozone that is generated as plasma is irradiated to the human body.

The suction fan may suck ozone based on the input from the user. According to an example embodiment, when the suction fan operates, ozone may be sucked into the first gripping portion 100 through a plurality of suction holes formed in the first operating portion 200. When plasma is irradiated to the skin, odor may occur in addition to ozone. The suction fan may also suck the odor to prevent the odor from reaching a customer.

The ozone filter may remove the sucked ozone. The ozone filter may be, for example, a mesh filter capable of absorbing ozone. Alternatively, the ozone filter may be formed using a plurality of carbon beads. The ozone filter may insert into the filter case and be fixed within the first operating portion 200.

The first operating portion 200 may be provided at one end of the first gripping portion 100 such that plasma may be discharged over a predetermined area. That is, the first plasma generating device 1000 may be a device for irradiating plasma over a large area.

In detail, the first operating portion 200 may include the plurality of pins for irradiating plasma to the human body. Here, the plurality of pins may be members that induce plasma generated from the plasma generating portion provided to the first gripping portion 100 to be irradiated to the skin. For example, one end of each of the plurality of pins may be connected to the plasma generating portion to receive voltage. Another end of each of the plurality of pins extending from one end may be provided towards the human body. When the voltage is applied to one end of each of the plurality of pins, plasma may be generated between an end of each of the plurality of pins and the skin of the human body.

The plurality of pins may be formed in one region to irradiate plasma to the human body. For example, the first operating portion 200 may include nine pins having a 3×3 matrix structure. As another example, the first operating portion 200 may include 16 pins having a 4×4 matrix structure. As another example, the first operating portion 200 may include 12 pins having a 3×4 matrix structure. The number of pins may vary within a range that may be easily changed by a person skilled in the art. The first operating portion 200 may irradiate plasma to a region that faces the plurality of pins. An example of the first operating portion 200 is described below with reference to FIGS. 4 to 8.

According to some example embodiments of the present disclosure, the skin care device 10000 may further include the skin cooling device 3000, the second plasma generating device, and the third plasma generating device. Each of the first plasma generating device 1000 to the third plasma generating device and the skin cooling device 3000 may include a different operating portion. The user may perform an appropriate procedure on a customer through devices having different operating portions.

According to the aforementioned configuration, the first plasma generating device 1000 may include the first gripping portion 100 and the first operating portion 200. The user may irradiate plasma to a predetermined area through the first plasma generating device 1000 including the first operating portion 200. Hereinafter, an example of the first operating portion 200 according to the present disclosure is described with reference to FIGS. 4 to 8.

Figure 4:
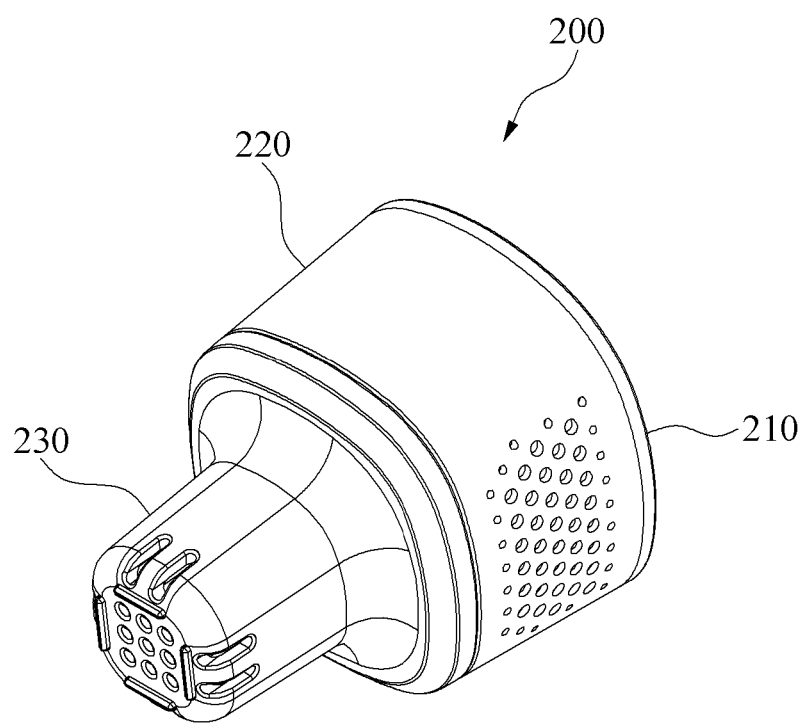
FIG. 4 is a perspective view illustrating an example of a first operating portion according to some example embodiments of the present disclosure.
Figure 5:
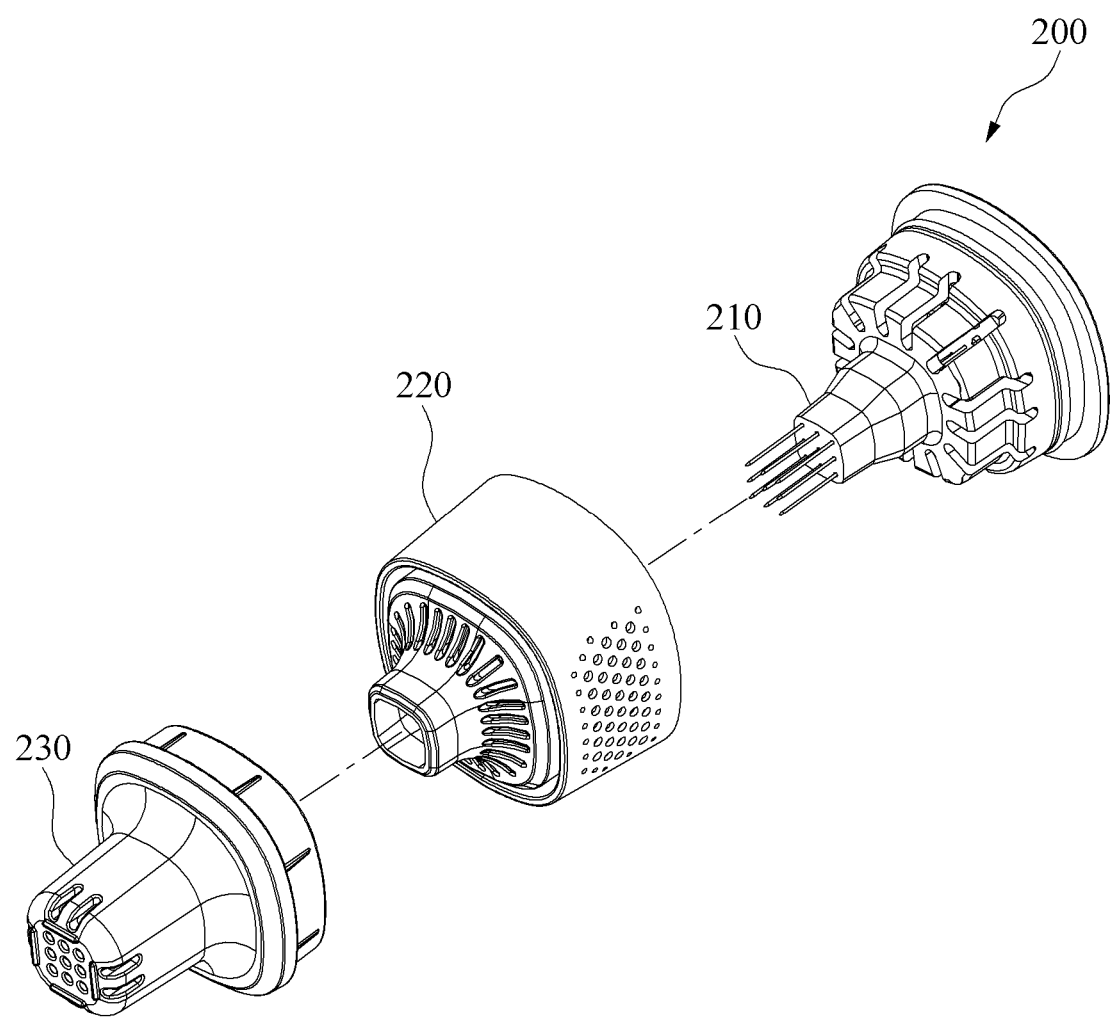
FIG. 5 is an exploded perspective view illustrating an example of a first operating portion according to some example embodiments of the present disclosure.

FIG. 4 is a perspective view illustrating an example of a first operating portion according to some example embodiments of the present disclosure. FIG. 5 is an exploded perspective view illustrating an example of a first operating portion according to some example embodiments of the present disclosure.

Referring to FIGS. 4 and 5, the first operating portion 200 may include a first housing 210, a second housing 220, and a third housing 230.

The first housing 210 may include a plurality of pins for irradiating plasma to the human body. The first housing 210 may couple to the second housing 220. When the first housing 210 couples to the second housing 220, the plurality of pins provided to the first housing 210 may pass through a hollow provided to the second housing 220.

The first housing 210 may detachably couple to the first gripping portion 100. For example, the first housing 210 may include at least one groove configured to couple to at least one protrusion provided to the first gripping portion 100.

According to some example embodiments of the present disclosure, the first housing 210 may include a first connecting portion to which a second air hose is connected. Here, the second air hose may be a hose for sucking ozone that is generated as plasma is irradiated to the human body. The second air hose may be a hose that is provided within the first gripping portion 100.

In detail, when plasma is irradiated to the skin, ozone that has adverse effect on a human may be generated. To prevent this, the air pump may be provided to the main body 2000 to which the first plasma generating device 1000 is connected. The first operating portion 200 may suck ozone through the second air hose that is connected to the first housing 210. Accordingly, ozone that may have adverse effect on a human may be removed. An example of connecting the second air hose to the first housing 210 is described below with reference to FIG. 9.

The second housing 220 may couple to the first housing 210. When the second housing 220 couples to the first housing 210, the hollow through which the plurality of pins may pass may be formed.

According to some example embodiments of the present disclosure, a plurality of suction holes through which ozone is sucked may be formed in the second housing 220. When the air pump provided to the main body 2000 operates, ozone may be sucked through the plurality of suction holes formed in the second housing 220.

According to some example embodiments of the present disclosure, the first gripping portion 100 may also include a suction fan for sucking ozone. Therefore, when the suction fan operates, ozone may be sucked through the plurality of suction holes formed in the second housing 220. In the present disclosure, the second housing 220 may include a plurality of discharge holes for discharging the sucked ozone. The plurality of discharge holes may be provided on the side of the second housing 220. An example of the second housing 220 is described below with reference to FIGS. 7A and 7B.

The third housing 230 may protect the plurality of pins from the outside through coupling to the second housing 220.

In detail, when the first housing 210 couples to the second housing 220, the plurality of pins provided to the first housing 210 may pass through the second housing 220 and be located outside. Each of the plurality of pins may be formed in a sharp shape to discharge plasma. Accordingly, the plurality of pins may be easily damaged by an external force from the outside. Therefore, the first operating portion 200 may protect the plurality of pins from the outside through the third housing 230.

According to some example embodiments of the present disclosure, the third housing 230 may be formed of a transparent material. For example, the third housing 230 may be formed of a transparent plastic material. For example, the third housing 230 may be formed of a material, such as acrylic, polypropylene (PP), polyethylene terephthalate (PET), polystyrene (PS), and polycarbonate (PC). Therefore, the user may easily verify locations of the plurality of pins with the naked eye and may perform a procedure on an exact portion.

According to some example embodiments of the present disclosure, the third housing 230 may include at least one space maintaining portion for maintaining a space between the first operating portion 200 and the human body.

For example, at least one space maintaining portion may protrude from one surface of the third housing 230 on which the third housing 230 faces the human body. Therefore, a space between the plurality of pins provided to the first housing 210 and the human body may be maintained. If the space between the plurality of pins for generating plasma and the human body is not appropriately maintained, the human body may be injured by the discharged plasma. Therefore, the third housing 230 may include the at least one space maintaining portion for maintaining the space between the plurality of pins and the human body. An example of the space maintaining portion according to the present disclosure is described below with reference to FIG. 8.

According to some example embodiments of the present disclosure, the third housing 230 may detachably couple to the second housing 220.

In detail, the third housing 230 may come into direct contact with the skin of a customer. If a procedure is performed on a first customer and then a procedure is performed using the same housing, the second customer may feel uncomfortable in terms of hygiene. Therefore, if necessary, the user may replace the third housing 230 that is configured to detachably couple to the second housing 220 or the first housing 210.

Hereinafter, each of the first housing 210, the second housing 220, and the third housing 230 according to the present disclosure will be described.

Figure 6A:
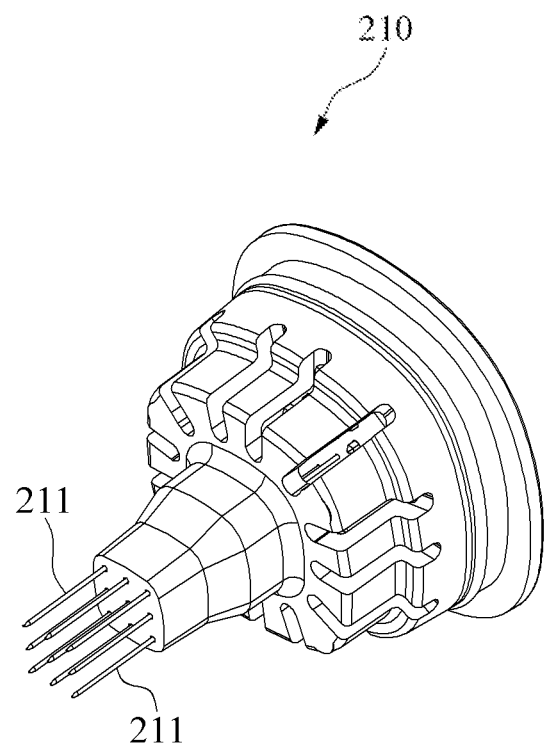
FIGS. 6A and 6B illustrates an example of a first housing according to some example embodiments of the present disclosures.
Figure 6B:
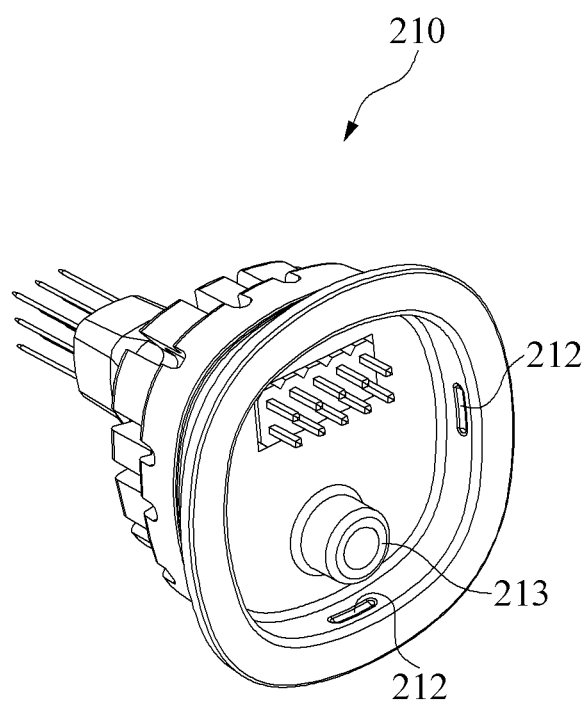

FIGS. 6A and 6B illustrates an example of a first housing according to some example embodiments.

Referring to FIG. 6A and FIG. 6B, the first housing 210 may include a plurality of pins 211, at least one groove 212, and a first connecting portion 213.

The plurality of pins 211 may induce plasma generated by the plasma generating portion of the first gripping portion 100 to the skin. According to an example embodiment, one end of each of the plurality of pins 211 may be connected to the plasma generating portion to receive voltage. Another end of each of the plurality of pins 211 extending from one end may be provided towards the human body. When voltage is applied to one end of each of the plurality of pins 211, plasma may be generated between an end of each of the plurality of pins 211 and the skin of the human body.

The plurality of pins 211 may be formed in one region to irradiate plasma to the human body. For example, the first housing 210 may include nine pins having a 3×3 matrix structure. As another example, the first housing 210 may include 16 pins having a 4×4 matrix structure. As another example, the first housing 210 may include 12 pins having a 3×4 matrix structure. The first operating portion 200 may irradiate plasma to a region that faces the plurality of pins 211.

The at least one groove 212 may couple to at least one protrusion provided to the first gripping portion 100. The first housing 210 may easily couple to or decouple from the first gripping portion 100 through the at least one groove 212.

The second air hose may be connected to the first connecting portion 213 such that ozone may be sucked through the air pump provided to the main body 2000. One end of the second air hose may be connected to the first connecting portion 213 and another end thereof may be connected to the first air hose 2200 that extends from the main body 2000. As the second air hose is connected to the first connecting portion 213, the air pump may suck ozone through the first air hose 2200 and the second air hose. An example of the first air hose 2200 and the second air hose according to the present disclosure is described below with reference to FIG. 9.

Figure 7A:
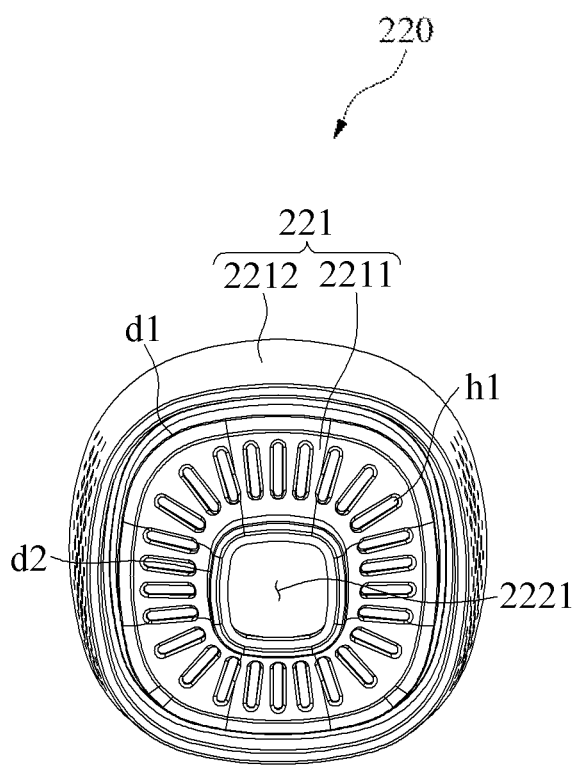
FIGS. 7A and 7B illustrates an example of a second housing according to some example embodiments of the present disclosures.
Figure 7B:
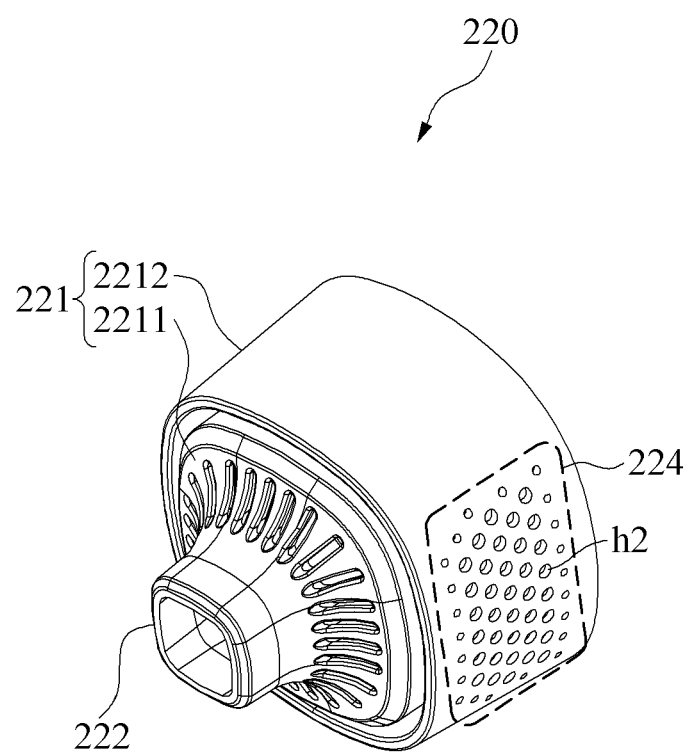

FIGS. 7A and 7B illustrates an example of a second housing according to some example embodiments of the present disclosure.

Referring to FIGS. 7A and 7B, the second housing 220 may include a case portion 221 and a protruding portion 222.

The case portion 221 may form at least a portion of an outer appearance of the second housing 220. In detail, the case portion 221 may include a first surface 2211 and a second surface 2212.

The first surface 2211 may form one surface in a direction in which the third housing 230 is located. A plurality of suction holes (h1) through which ozone is sucked may be formed in the first surface 2211. According to an example embodiment, each of the plurality of suction holes (h1) may be formed as a slot.

In detail, the first gripping portion 100 according to the present disclosure may include a suction fan for sucking ozone. When the suction fan operates, ozone that is generated as plasma is irradiated to the skin may be sucked through the plurality of suction holes (h1).

The second surface 2212 may extend from a first circumference (d1) of the first surface 2211 in a direction opposite to the direction in which the third housing 230 is located. The second surface 2212 may extend in a direction orthogonal to the first surface 2211. For example, the second surface 2212 may form the side surface of the second housing 220.

Herein, a groove into which at least a portion of the third housing 230 inserts may be formed between the first surface 2211 and the second surface 2212. For example, the groove may be recessed in a direction opposite to the direction in which the third housing 230 is located from the first circumference (d1) of the first surface 2211.

The second surface 2212 may include a plurality of discharge holes (h2) formed in at least one region 224 to discharge ozone sucked through the at least one suction hole (h1).

In detail, the first gripping portion 100 may include the suction fan for sucking ozone. When the suction fan operates, ozone that is generated as plasma is irradiated to the skin may be sucked through the plurality of suction holes (h1). Ozone sucked through the plurality of suction holes (h1) may be discharged through the plurality of discharge holes (h2). The plurality of discharge holes (h2) may be formed in at least one region 224 of the second surface 2212 orthogonal to the skin. Therefore, ozone discharged through the plurality of discharge holes (h2) may not be directly directed to a customer undergoing a procedure.

The protruding portion 222 may protrude from the first surface 2211.

The protruding portion 222 may protrude from the first surface 2211 to have a second circumference (d2) less than the first circumference (d1) of the first surface 2211. A hollow 2221 through which the plurality of pins 211 provided to the first housing 210 pass may be provided to the protruding portion 222. According to an example embodiment, the hollow 2221 may be provided to correspond to an area formed by the plurality of pins 211. For example, the hollow 2221 may be formed to have a greater diameter than the area formed by the plurality of pins 211.

Herein, a curved surface may be present between the first surface 2211 and the protruding portion 222. The plurality of suction holes (h1) may be located on the curved surface.

Figure 8:
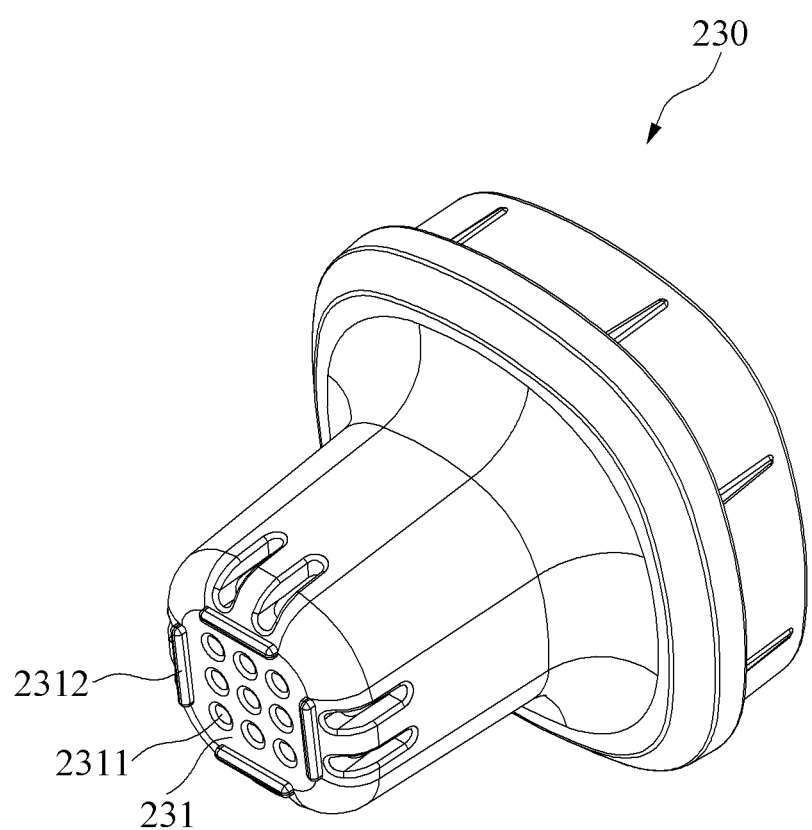
FIG. 8 is a perspective view illustrating an example of a third housing according to some example embodiments of the present disclosure.

FIG. 8 is a perspective view illustrating an example of a third housing according to some example embodiments of the present disclosure.

Referring to FIG. 8, the third housing 230 may include a third surface 231. The third surface 231 may be a surface that faces the human body when the user performs a procedure on the human body.

The third surface 231 may include a plurality of holes 2311 and at least one space maintaining portion 2312.

Herein, the number of the plurality of holes 2311 may correspond to the number of the plurality of pins 211. For example, if the number of pins provided to the first housing 210 is nine, the number of holes formed in the third surface 231 may be nine. As another example, if the number of pins provided to the first housing 210 is 16, the number of holes formed in the third surface 231 may be 16. As the number of the plurality of holes 2311 is formed to correspond to the number of the plurality of pins 211, plasma discharged from the plurality of pins 211 may be irradiated to the human body.

The at least one space maintaining portion 2312 may protrude from the third surface 231 to maintain a space between the third surface 231 and the human body. If the space between the plurality of pins 211 through which plasma is discharged and the human body is not appropriately maintained, the human body may be injured by the discharged plasma. Therefore, the at least one space maintaining portion 2312 for maintaining the space between the plurality of pins 211 and the human body may protrude from the third surface 231.

According to some example embodiments of the present disclosure, the third housing 230 may be formed of a transparent material. For example, the third housing 230 may be formed of a material, such as acrylic, polypropylene (PP), polyethylene terephthalate (PET), polystyrene (PS), and polycarbonate (PC). Therefore, the user may easily verify locations of the plurality of pins 211 with the naked eye and may perform a procedure on an exact portion.

As described above with reference to FIGS. 6 to 8, the first operating portion 200 may include the first housing 210, the second housing 220, and the third housing 230. The first housing 210 may include the plurality of pins 211 capable of irradiating plasma to the human body. The second housing 220 may include the plurality of suction holes (h1) for sucking ozone that is generated as plasma is irradiated to the human body. The second housing 220 may include the plurality of discharge holes (h2) for discharging the sucked ozone. The third housing 230 may maintain the space between the plurality of pins 211 and the human body. The first operating portion 200 may allow the user to perform an appropriate procedure through organic coupling of the first housing 210, the second housing 220, and the third housing 230.

According to some example embodiments of the present disclosure, the first plasma generating device 1000 may include the second air hose. One end of the second air hose may be connected to the first connecting portion 213 of the first housing 210 and another end thereof may be connected to the first air hose 2200 extending from the main body 2000. Therefore, the air pump provided to the main body 2000 may suck ozone through the first air hose 2200 and the second air hose. Hereinafter, an example of the first air hose 2200 and the second air hose according to the present disclosure will be described.

Figure 9:
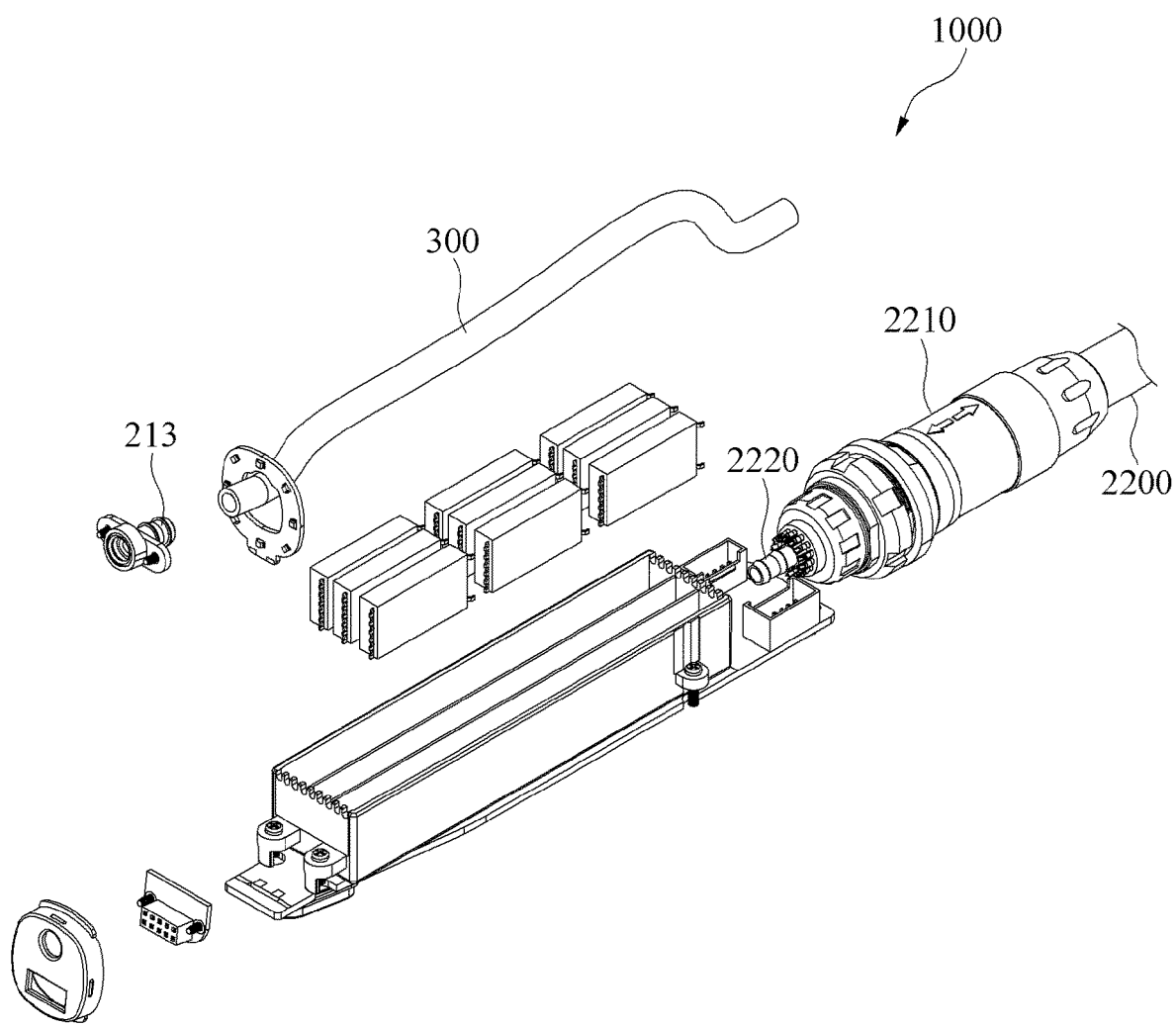
FIG. 9 is an exploded perspective view illustrating an example of a first air hose and a second air hose according to some example embodiments of the present disclosure.

FIG. 9 is an exploded perspective view illustrating an example of a first air hose and a second air hose according to some example embodiments of the present disclosure.

Referring to FIG. 9, the adaptor 2210 may be provided at one end of the first air hose 2200 that extends from the main body 2000. As described above, the first plasma generating device 1000 may include the fastener 120 to which the adaptor 2210 couples. In addition to the first plasma generating device 1000, each of the skin cooling device 3000, the second plasma generating device, and the third plasma generating device may include the fastener. The user may detachably provide the first air hose 2200 to the first plasma generating device 1000 through the fastener 120 and the adaptor 2210.

In response to coupling of the fastener 120 and the adaptor 2210, a second connecting portion 2220 provided at one end of the fastener 120 may insert into one end of a second air hose 300 provided to the first gripping portion 100 of the first plasma generating device 1000. That is, the second connecting portion 2220 may couple to the second air hose 300. Another end of the second air hose 300 may couple to the first connecting portion 213 provided to the first housing 210. Accordingly, when the first air hose 2200 couples to the first plasma generating device 1000, the air pump provided to the main body 2000 may suck ozone that is generated as the first operating portion 200 operates.

According to some example embodiments of the present disclosure, the skin care device 10000 may further include the skin cooling device 3000, the second plasma generating device, and the third plasma generating device. Hereinafter, plasma generating devices according to the present disclosure are described with reference to FIGS. 10 to 12.

Figure 10:
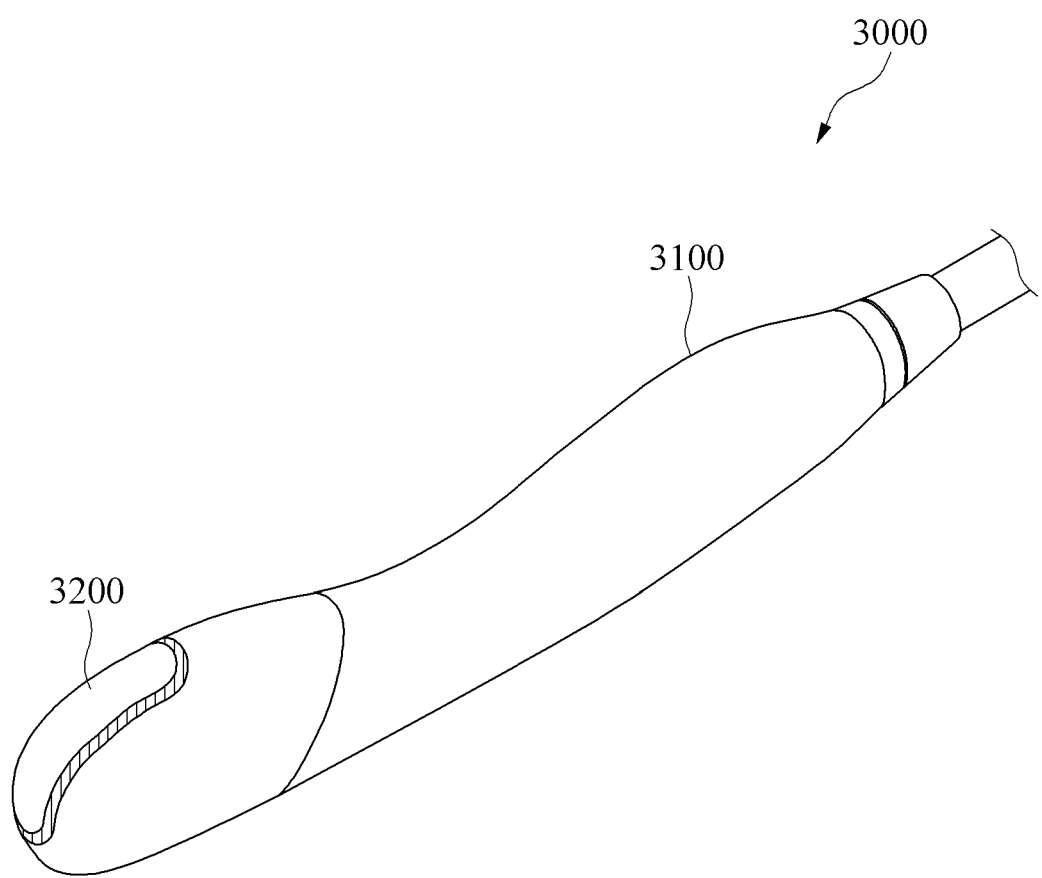
FIG. 10 is a perspective view illustrating an example of a skin cooling device according to some example embodiments of the present disclosure.

FIG. 10 is a perspective view illustrating an example of a skin cooling device according to some example embodiments of the present disclosure.

Referring to FIG. 10, the skin cooling device 3000 may include a second gripping portion 3100 and a second operating portion 3200. The second gripping portion 3100 may be formed in a shape capable of being gripped by the user. The second gripping portion 3100 may be formed in a shape that allows the user to easily grip the skin cooling device 3000. According to an example embodiment, the second gripping portion 3100 may be detachably connected to the main body 2000. For example, the second gripping portion 3100 may be connected to the first air hose 2200 of the main body 2000 through a fastener provided at its one end.

The second operating portion 3200 may cool the human body through a Peltier element that generates Peltier effect. Here, the Peltier effect may be effect in which cooling occurs since electrons carry energy required to move from one metal surface to the other metal surface when current flows in a loop formed by mutually grounding metals through a semiconductor. The Peltier element may be an electronic material using the Peltier effect. The Peltier element according to the present disclosure may use the conventional art and thus, further description is omitted.

The user may couple the skin cooling device 3000 to the main body 2000 before irradiating plasma to the human body using the first plasma generating device 1000. The user may cool one region of the human body to which plasma is to be irradiated through the skin cooling device 3000. After performing such cooling, the user may separate the skin cooling device 3000 and may connect the first plasma generating device 1000 and the main body 2000. The user may irradiate plasma to the human body through the first plasma generating device 1000 and then may separate the first plasma generating device 1000. The user may connect the skin cooling device 3000 and the main body 2000 and may cool one region of the human body to which plasma is irradiated.

Figure 11:
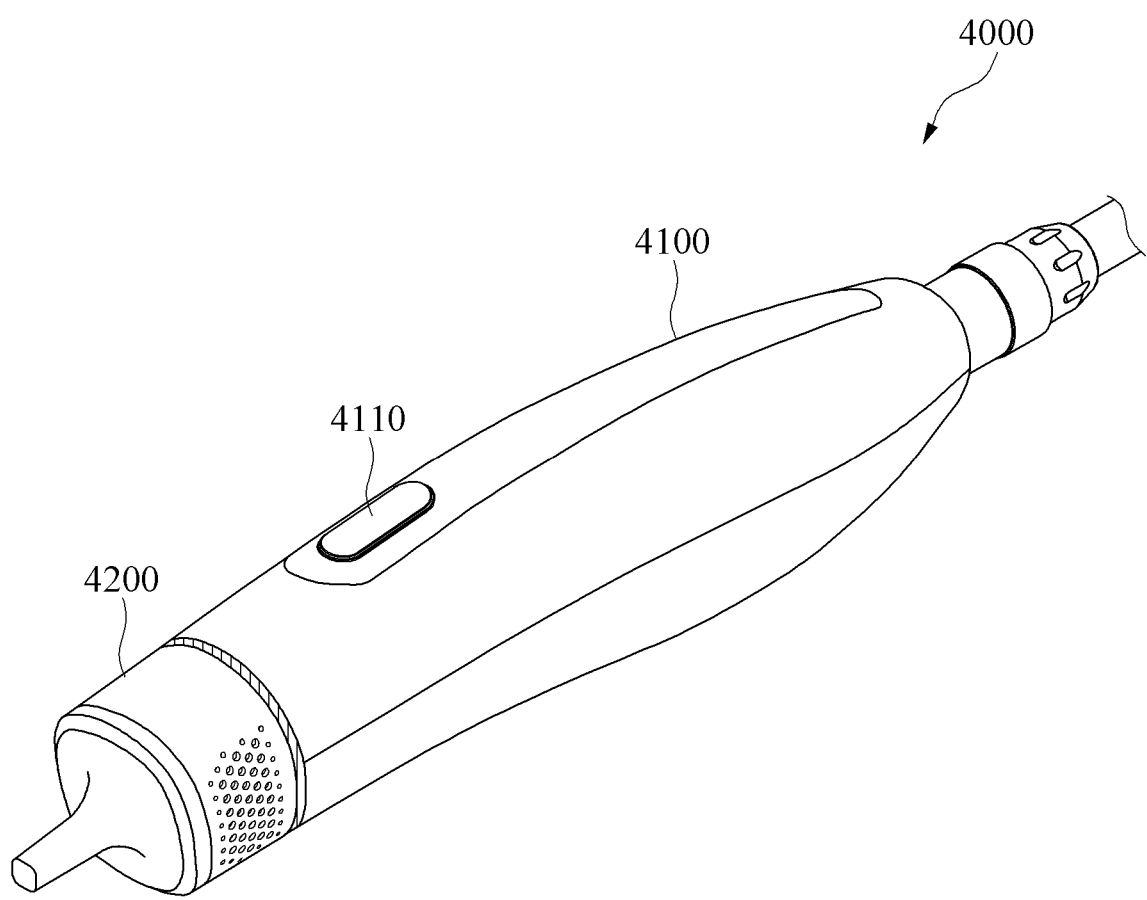
FIG. 11 is a perspective view illustrating an example of a second plasma generating device according to some example embodiments of the present disclosure.

FIG. 11 is a perspective view illustrating an example of a second plasma generating device according to some example embodiments of the present disclosure.

Referring to FIG. 11, a second plasma generating device 4000 may include a third gripping portion 4100 and a third operating portion 4200. The third gripping portion 4100 may be formed in a shape capable of being gripped by the user. The third gripping portion 4100 may be formed in a shape that allows the user to easily grip the second plasma generating device 4000. According to an example embodiment, the third gripping portion 4100 may be detachably connected to the main body 2000. For example, the third gripping portion 4100 may be connected to the first air hose 2200 of the main body 2000 through a fastener provided at its one end.

The second plasma generating device 4000 may be a plasma generating device for irradiating plasma to a local area of the human body. For example, the third operating portion 4200 of the second plasma generating device 4000 may include a single pin for irradiating plasma to the human body. Therefore, the second plasma generating device 4000 may discharge plasma to the local area of the human body.

According to some example embodiments of the present disclosure, output of plasma discharged through the second plasma generating device 4000 may be higher than output of plasma discharged through the first plasma generating device 1000. For example, the first plasma generating device 1000 may generate plasma by applying voltage to a plurality of pins through a plurality of transformers provided to a plasma generating portion. The second plasma generating device 4000 may generate plasma by applying voltage to a single pin through a plurality of transformers. Therefore, output of plasma discharged through the second plasma generating device 4000 may be higher than output of plasma discharged through the first plasma generating device 1000. The user may perform a procedure by selecting an appropriate plasma generating device between the first plasma generating device 1000 and the second plasma generating device 4000 according to a condition of a treatment site. For example, when the user needs to perform a procedure that requires precision, the user may perform the procedure by coupling the second plasma generating device 4000 to the main body 2000. As another example, when the user needs to perform a procedure that requires high power, the user may perform the procedure by coupling the second plasma generating device 4000 to the main body 2000. As another example, when the user needs to perform a procedure on a large area, the user may perform the procedure by coupling the first plasma generating device 1000 to the main body 2000.

Figure 12:
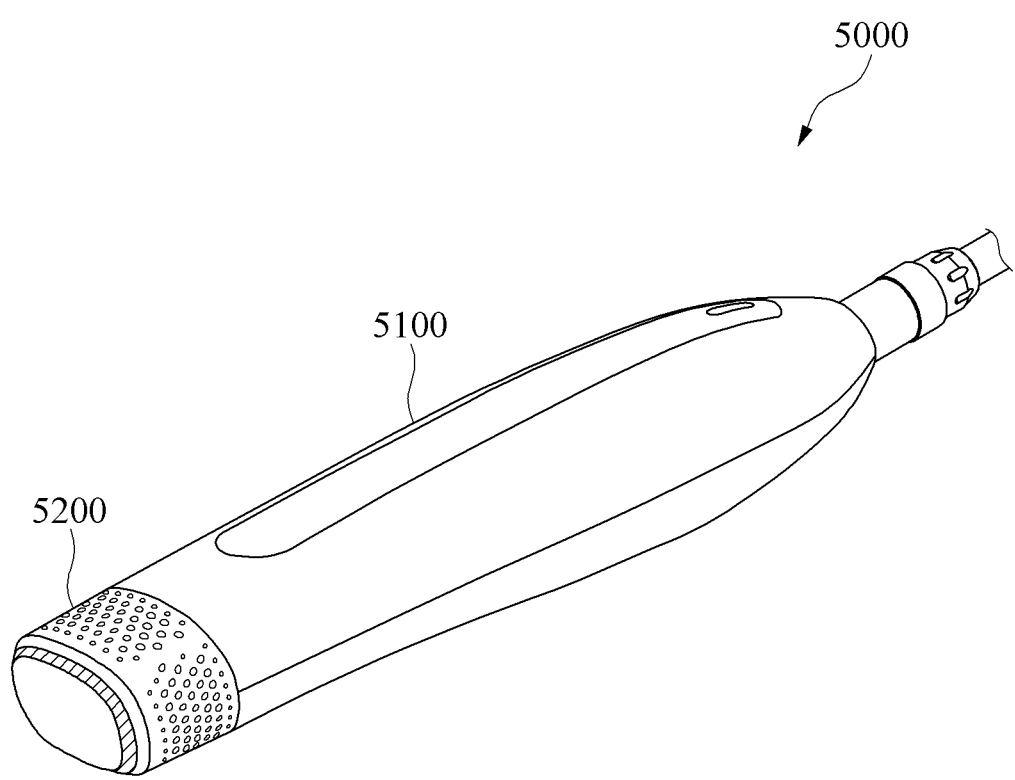
FIG. 12 is a perspective view illustrating an example of a third plasma generating device according to some example embodiments of the present disclosure.

FIG. 12 is a perspective view illustrating an example of a third plasma generating device according to some example embodiments of the present disclosure.

Referring to FIG. 12, a third plasma generating device 5000 may include a fourth gripping portion 5100 and a fourth operating portion 5200. The fourth gripping portion 5100 may be formed in a shape capable of being gripped by the user. The fourth gripping portion 5100 may be formed in a shape that allows the user to easily grip the third plasma generating device 5000. According to an example embodiment, the fourth gripping portion 5100 may be detachably connected to the main body 2000. For example, the fourth gripping portion 5100 may be connected to the first air hose 2200 of the main body 2000 through a fastener provided at its one end.

The third plasma generating device 5000 may irradiate plasma to a wider area than the first plasma generating device 1000. The fourth operating portion 5200 of the third plasma generating device 5000 may include a ceramic plate for irradiating plasma. Alternatively, the fourth operating portion 5200 may include a dielectric made of a porous material, such as ceramic or glass. The fourth operating portion 5200 may discharge plasma to a larger area through a ceramic plate. The fourth operating portion 5200 may discharge plasma with weaker output than the first plasma generating device 1000 and the second plasma generating device 4000 through the ceramic plate. When a procedure, such as sterilization or pasteurization, is required, the user may perform a procedure by connecting the third plasma generating device 5000 to the main body 2000.

Description related to the proposed example embodiments is provided such that one skilled in the art may use or implement the present disclosure. It will be apparent to one skilled in the art that various modifications may be made to the example embodiments without departing from the scope of the present disclosure. Herein, the general principles may be applied to other example embodiments without departing from the scope of the present disclosure. Therefore, the present disclosure is not limited to the example embodiments and should be interpreted within the widest scope consistent with the principles and novel features presented herein.

What is claimed is:

1. A skin care device using plasma, the skin care device comprising:
    a first plasma generating device; and
    a main body configured to supply power to the first plasma generating device and to control the first plasma generating device based on an input from a user,
    wherein the first plasma generating device comprises:
    a first gripping portion configured to detachably connect to the main body, comprising a plasma generating portion for generating the plasma, and formed in a shape capable of being gripped by the user; and
    a first operating portion provided at one end of the first gripping portion and configured to emit the plasma over a predetermined area,
    wherein the first operating portion comprises:
    a first housing having a plurality of pins for irradiating the plasma to a human body;
    a second housing to which the first housing couples, and formed with a hollow through which the plurality of pins pass in response to coupling of the first housing; and
    a third housing configured to couple to the second housing and protect the plurality of pins from an outside,
    the plasma generating portion comprises:
    a switch unit comprising a plurality of electrodes and configured to control the plurality of electrodes based on an input from the user;
    a plurality of transformers configured to boost voltage transmitted from the plurality of electrodes;
    a transformer case, wherein the plurality of transformers are inserted into the transformer case; and
    a plasma padder configured to transmit the voltage boosted by the plurality of transformers to the plurality of pins.

2. The skin care device of claim 1, wherein the main body comprises:
    a first interface unit configured to receive an input from the user; and
    a first ozone removal portion configured to remove ozone (O3) that is generated as the plasma is irradiated to the human body.

3. The skin care device of claim 2, wherein the first ozone removal portion comprises:
    an air pump configured to suck the ozone; and
    a first air hose of which one end is connected to the air pump and of which another end is connected to a second air hose provided to the first plasma generating device.

4. The skin care device of claim 3, wherein the first gripping portion further comprises a fastener configured to detachably connect the first air hose.

5. The skin care device of claim 1, wherein the number of the plurality of transformers is less than or equal to the number of the plurality of pins.

6. The skin care device of claim 1, wherein the switch unit is configured to apply voltage to at least one transformer through at least some electrodes among the plurality of electrodes based on an input from the user, and
    the at least one transformer is configured to boost the applied voltage and to transmit the boosted voltage to at least one pin through the plasma padder.

7. The skin care device of claim 1, wherein the first gripping portion further comprises a second ozone removal portion configured to remove ozone that is generated as the plasma is irradiated to the human body.

8. The skin care device of claim 7, wherein the second ozone removal portion comprises:
    a suction fan configured to suck the ozone; and
    an ozone filter configured to remove the sucked ozone.

9. The skin care device of claim 8, wherein the second housing comprises:
    a case portion configured to form at least a portion of an outer appearance of the second housing, the case portion comprising a first surface that forms one surface in a direction in which the third housing is located and a second surface that extends from a first circumference of the first surface in a direction opposite to the direction in which the third housing is located; and
    a protruding portion configured to protrude from the first surface, the protruding portion protruding from the first surface to have a second circumference less than the first circumference of the first surface.

10. The skin care device of claim 9, wherein the hollow formed to allow the plurality of pins to pass is provided to the protruding portion,
    a plurality of suction holes through which the ozone is sucked as the suction fan operates are formed in the first surface, and
    a plurality of discharge holes through which the ozone is discharged are formed in at least one region of the second surface.

11. The skin care device of claim 1, wherein the third housing is formed with a plurality of holes formed in a third surface that faces the human body, such that the plasma emitted from the plurality of pins is irradiated to the human body.

12. The skin care device of claim 11, wherein the number of the plurality of holes corresponds to the number of the plurality of pins.

13. The skin care device of claim 11, wherein the third housing comprises at least one space maintaining portion configured to protrude from the third surface and to maintain a space between the third surface and the human body.

14. The skin care device of claim 1, further comprising:
    a skin cooling device comprising a second operating portion configured to detachably couple to the main body and to cool the human body through a Peltier element that generates Peltier effect.

15. The skin care device of claim 1, further comprising:
    a second plasma generating device comprising a plasma generating portion configured to detachably couple to the main body and to generate plasma, a third gripping portion formed in a shape capable of being gripped by the user, and a third operating portion provided at one end of the third gripping portion and configured to emit the plasma to one point.

* * * * *